(12) United States Patent
David et al.

(10) Patent No.: US 9,649,743 B2
(45) Date of Patent: May 16, 2017

(54) DYNAMICALLY TRACKING SPECTRUM FEATURES FOR ENDPOINT DETECTION

(71) Applicant: Applied Materials, Inc., Santa Clara, CA (US)

(72) Inventors: Jeffrey Drue David, San Jose, CA (US); Harry Q. Lee, Los Altos, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 14/995,097

(22) Filed: Jan. 13, 2016

(65) Prior Publication Data

US 2016/0129550 A1 May 12, 2016

Related U.S. Application Data

(63) Continuation of application No. 14/331,534, filed on Jul. 15, 2014, now Pat. No. 9,283,653, which is a
(Continued)

(51) Int. Cl.
 *B24B 37/00* (2012.01)
 *B24B 49/12* (2006.01)
(Continued)

(52) U.S. Cl.
 CPC ............ *B24B 49/12* (2013.01); *B24B 37/013* (2013.01); *B24B 37/205* (2013.01); *G01N 21/25* (2013.01)

(58) Field of Classification Search
 CPC ..... B24B 49/12; B24B 37/013; B24B 37/205; B24B 37/228; H01L 21/304
(Continued)

(56) References Cited

U.S. PATENT DOCUMENTS

| 5,559,428 A | 9/1996 | Li et al. |
| 5,659,492 A | 8/1997 | Li et al. |

(Continued)

FOREIGN PATENT DOCUMENTS

| JP | H11-325840 | 11/1999 |
| JP | 2000-040680 | 2/2000 |

(Continued)

OTHER PUBLICATIONS

Kim, Sang-Taek, Authorized Officer, International Search Report and Written Opinion of PCT Application No. PCT/US2011/033258 mailed Jan. 11, 2012, 9 pages.

(Continued)

*Primary Examiner* — George Nguyen
(74) *Attorney, Agent, or Firm* — Fish & Richardson P.C.

(57) ABSTRACT

A method of controlling polishing includes polishing a substrate and receiving an identification of a selected spectral feature, a wavelength range having a width, and a characteristic of the selected spectral feature to monitor during polishing. A sequence of spectra of light from the substrate is measured while the substrate is being polished. A sequence of values of the characteristic of the selected spectral feature is generated from the sequence of spectra. For at least some spectra from the sequence of spectra, a modified wavelength range is generated based on a position of the spectral feature within a previous wavelength range used for a previous spectrum in the sequence of spectra, the modified wavelength range is searched for the selected spectral feature, and a value of a characteristic of the selected spectral feature is determined.

20 Claims, 10 Drawing Sheets

Related U.S. Application Data continuation of application No. 13/090,926, filed on Apr. 20, 2011, now Pat. No. 8,834,229.

(60) Provisional application No. 61/331,751, filed on May 5, 2010.

(51) Int. Cl.
  *B24B 37/013* (2012.01)
  *B24B 37/20* (2012.01)
  *G01N 21/25* (2006.01)

(58) Field of Classification Search
  USPC .............................. 451/5, 6, 41, 11, 285–290
  See application file for complete search history.

(56) References Cited

U.S. PATENT DOCUMENTS

| | | | |
|---|---|---|---|
| 6,020,968 A | 2/2000 | Horie | |
| 6,078,417 A | 6/2000 | Perino et al. | |
| 6,106,662 A | 8/2000 | Bibby | |
| 6,153,116 A | 11/2000 | Yang | |
| 6,160,621 A | 12/2000 | Perry | |
| 6,276,987 B1 | 8/2001 | Li | |
| 6,361,646 B1 | 3/2002 | Bibby et al. | |
| 6,491,569 B2 | 12/2002 | Bibby, Jr. et al. | |
| 6,609,086 B1 | 8/2003 | Bao et al. | |
| 6,645,045 B2 | 11/2003 | Ohkawa | |
| 6,664,557 B1 | 12/2003 | Amartur | |
| 8,039,397 B2 | 10/2011 | David et al. | |
| 8,260,446 B2 | 9/2012 | David et al. | |
| 8,834,229 B2 | 9/2014 | David et al. | |
| 9,283,653 B2 * | 3/2016 | David .................. | B24B 37/013 |
| 2002/0115380 A1 | 8/2002 | Yamane et al. | |
| 2002/0127950 A1 | 9/2002 | Hirose et al. | |
| 2002/0127951 A1 | 9/2002 | Ishikawa et al. | |
| 2002/0155789 A1 | 10/2002 | Bibby et al. | |
| 2004/0092209 A1 | 5/2004 | Schneegans et al. | |
| 2007/0254557 A1 | 11/2007 | Kobayashi et al. | |
| 2008/0099443 A1 | 5/2008 | Benvegnu et al. | |
| 2009/0036026 A1 | 2/2009 | David et al. | |
| 2009/0233525 A1 | 9/2009 | Ueda et al. | |
| 2010/0093260 A1 | 4/2010 | Kobayashi et al. | |
| 2010/0106456 A1 | 4/2010 | Genio et al. | |
| 2011/0275281 A1 | 11/2011 | David et al. | |

FOREIGN PATENT DOCUMENTS

| | | |
|---|---|---|
| JP | 2001-345299 | 12/2001 |
| JP | 2002-359217 | 12/2002 |
| JP | 2004-017229 | 1/2004 |
| JP | 2009-505847 | 2/2009 |
| JP | 2009-283868 | 12/2009 |
| KR | 10-2008-0042895 | 5/2008 |
| WO | WO2007/024807 | 3/2007 |

OTHER PUBLICATIONS

Search Report in Taiwan Application No. 100114087, dated Apr. 7, 2014, 2 pages (with English translation).
Office Action in Chinese Application No. 201180022552.7, dated Dec. 16, 2014, 17 pages (with English translation).
Office Action in Japanese Application No. 2013-509099, dated Jul. 7, 2015, 4 pages (with English analysis).
Office Action in Chinese Application No. 201180022552.7, dated Aug. 17, 2015, 11 pages (with English Translation).
Japanese Office Action in Japanese Application No. 2013-509099, dated Jun. 14, 2016, 6 pages (English Translation).
Japanese Office Action in Japanese Application No. 2015-242126, dated Oct. 11, 2016, 8 pages (English Translation).
Korean Office Action in Korean Application No. 10-2012-7031793, dated Nov. 16, 2016, 10 pages (English Summary).

* cited by examiner

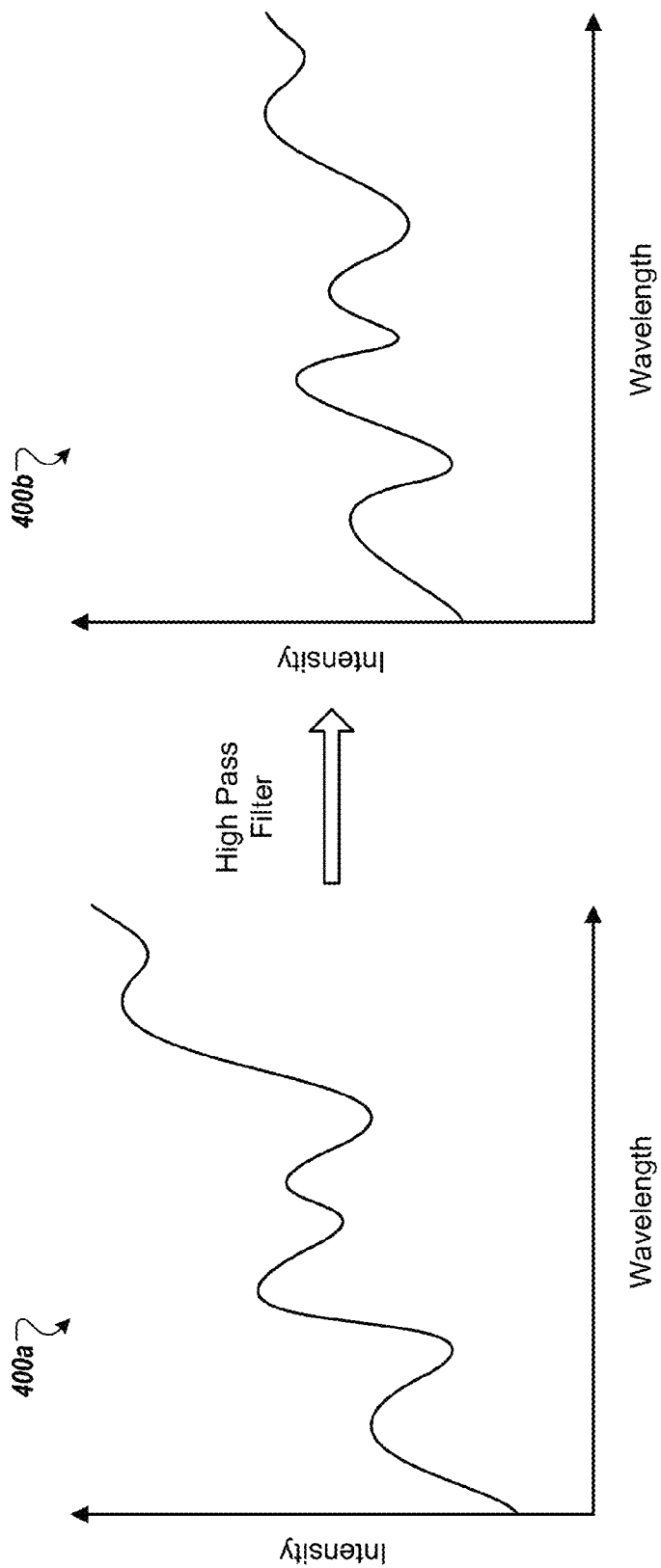

DYNAMICALLY TRACKING SPECTRUM FEATURES FOR ENDPOINT DETECTION

CROSS-REFERENCE TO RELATED APPLICATIONS

This application is a continuation of U.S. patent application Ser. No. 14/331,534, filed Jul. 15, 2014, which is a continuation of U.S. patent application Ser. No. 13/090,926, filed Apr. 20, 2011, which claims the benefit of priority to U.S. Provisional Application Ser. No. 61/331,751, filed on May 5, 2010, the entire disclosures of which are incorporated herein by reference.

TECHNICAL FIELD

The present disclosure relates to optical monitoring during chemical mechanical polishing of substrates.

BACKGROUND

An integrated circuit is typically formed on a substrate by the sequential deposition of conductive, semiconductive, or insulative layers on a silicon wafer. One fabrication step involves depositing a filler layer over a non-planar surface and planarizing the filler layer. For certain applications, the filler layer is planarized until the top surface of a patterned layer is exposed. A conductive filler layer, for example, can be deposited on a patterned insulative layer to fill the trenches or holes in the insulative layer. After planarization, the portions of the conductive layer remaining between the raised pattern of the insulative layer form vias, plugs, and lines that provide conductive paths between thin film circuits on the substrate. For other applications, such as oxide polishing, the filler layer is planarized until a predetermined thickness is left over the non planar surface. In addition, planarization of the substrate surface is usually required for photolithography.

Chemical mechanical polishing (CMP) is one accepted method of planarization. This planarization method typically requires that the substrate be mounted on a carrier or polishing head. The exposed surface of the substrate is typically placed against a rotating polishing pad. The carrier head provides a controllable load on the substrate to push it against the polishing pad. An abrasive polishing slurry is typically supplied to the surface of the polishing pad.

One problem in CMP is determining whether the polishing process is complete, i.e., whether a substrate layer has been planarized to a desired flatness or thickness, or when a desired amount of material has been removed. Variations in the slurry distribution, the polishing pad condition, the relative speed between the polishing pad and the substrate, and the load on the substrate can cause variations in the material removal rate. These variations, as well as variations in the initial thickness of the substrate layer, cause variations in the time needed to reach the polishing endpoint. Therefore, the polishing endpoint cannot be determined merely as a function of polishing time.

In some systems, a substrate is optically monitored in-situ during polishing, e.g., through a window in the polishing pad. However, existing optical monitoring techniques may not satisfy increasing demands of semiconductor device manufacturers.

SUMMARY

Some optical endpoint detection systems track selected spectral feature characteristics in spectra measurements in order to determine endpoint or to change a polishing rate. In a spectrum, spectral features similar to the selected spectral feature can make it difficult to track the selected spectral feature. Identification of a wavelength range for the optical endpoint detection system to search for the selected spectral feature can allow the optical endpoint detection system to correctly identify the selected spectral feature, and with reduced processing resources.

In one aspect, a method of controlling polishing includes polishing a substrate and receiving an identification of a selected spectral feature, a wavelength range having a width, and a characteristic of the selected spectral feature to monitor during polishing. A sequence of spectra of light from the substrate is measured while the substrate is being polished. A sequence of values of the characteristic of the selected spectral feature is generated from the sequence of spectra. The generating includes for at least some spectra from the sequence of spectra, generating a modified wavelength range based on a position of the spectral feature within a previous wavelength range used for a previous spectrum in the sequence of spectra, searching the modified wavelength range for the selected spectral feature, and determining a value of a characteristic of the selected spectral feature. At least one of a polishing endpoint or an adjustment for a polishing rate based is determined on the sequence of values.

Implementations can include one or more of the following features. The wavelength range can have a fixed width. Generating the modified wavelength range can comprise centering the fixed width on the position of the characteristic in the previous wavelength range. Generating the modified wavelength range can include determining a position of the characteristic in the previous wavelength range and adjusting the wavelength range such that in the modified wavelength range the characteristic is positioned closer to a center of the modified wavelength range. Generating the modified wavelength range can include determining a wavelength value for the selected spectral feature for at least some of the spectra in the sequence of spectra to generate a sequence of wavelength values, fitting a function to the sequence of wavelength values, and calculating an expected wavelength value for the selected spectra feature for a subsequent spectrum measurement from the function. The function can be a linear function. Generating the modified wavelength range can include centering the width of the wavelength range on the expected wavelength value.

Implementations can include one or more of the following features. The method can comprise fitting a function to the sequence of values and determining at least one of a polishing endpoint or an adjustment for a polishing rate based on the function. Determining a polishing endpoint can include calculating an initial value of the characteristic from the function, calculating a current value of the characteristic from the function, and calculating a difference between the initial value and the current value, and ceasing polishing when the difference reaches a target difference. The function can be a linear function. The selected spectral feature can comprise a spectral peak, a spectral valley, or a spectral zero-crossing. The characteristic can comprise a wavelength, a width, or an intensity. The selected spectral feature can comprise a spectral peak and the characteristic can comprise a peak width. The spectra can be measured for visible light, and the wavelength range can have a width of between 50 and 200 nanometers.

In another aspect, a method of controlling polishing includes receiving user input selecting a fixed wavelength range that is a subset of wavelengths measured by an in-situ monitoring system, receiving an identification of a selected spectral feature and a characteristic of the selected spectral feature to monitor during polishing, polishing a substrate, measuring a sequence of spectra of light from the substrate while the substrate is being polished for each spectrum in the sequence of spectra, searching the fixed wavelength range of the each spectrum for the selected spectral feature, and determining a value of a characteristic of the selected spectral feature to generate a sequence of values, and determining at least one of a polishing endpoint or an adjustment for a polishing rate based on the sequence of values.

Implementations can include one or more of the following features. The in-situ monitoring system can measure intensity of wavelengths at least including visible light, and the fixed wavelength range can have a width of between 50 and 200 nanometers. The selected spectral feature can be a spectral peak, a spectral valley, or a spectral zero-crossing. The characteristic can be a wavelength, a width, or an intensity.

Implementations can optionally include one or more of the following advantages. Identification of a wavelength range to search for selected spectral feature characteristics can allow greater accuracy in detection of endpoint or determination of a polishing rate change, e.g., the system is less likely to select an incorrect spectral feature during subsequent spectra measurements. Tracking spectral features in a wavelength range instead across an entire spectrum allows the spectral features to be more easily and quickly identified. Processing resources needed to identify the selected spectral features can be reduced.

The details of one or more implementations are set forth in the accompanying drawings and the description below. Other aspects, features, and advantages will be apparent from the description and drawings, and from the claims.

BRIEF DESCRIPTION OF THE DRAWINGS

FIG. 4A shows an example graph of a spectrum of light reflected from a substrate.

FIG. 4B shows the graph of FIG. 4A passed through a high pass filter.

Like reference numbers and designations in the various drawings indicate like elements.

DETAILED DESCRIPTION

One optical monitoring technique is to measure spectra of light reflected from a substrate during polishing, and identify a matching reference spectra from a library. One potential problem with the spectrum matching approach is that for some types of substrates there are significant substrate-to-substrate differences in underlying die features, resulting in variations in the spectra reflected from substrates that ostensibly have the same outer layer thickness. These variations increase the difficulty of proper spectrum matching and reduce reliability of the optical monitoring.

One technique to counteract this problem is to measure spectra of light reflected off of substrates being polished and identify changes in spectral feature characteristics. Tracking changes in a characteristic of a feature of the spectrum, e.g., a wavelength of a spectral peak, can allow greater uniformity in polishing between substrates within a batch. By determining a target difference in the spectral feature characteristic, endpoint can be called when the value of the characteristic has changed by the target amount.

One potential problem while polishing a single substrate is the introduction of a spectral feature in a spectrum measurement that is similar to the spectral feature selected for tracking. In some implementations, a wavelength range is defined around the selected spectral feature when the spectral feature is initially identified. During a later spectrum measurement, the selected spectral feature is searched for in or close to the defined wavelength range instead of across the entire wavelength spectrum, making it easier to identify the selected spectral feature correctly.

Spectral features can include spectral peaks, spectral valleys, spectral inflection points, or spectral zero-crossings. Characteristics of the features can include a wavelength, a width, or an intensity.

Figure 1:
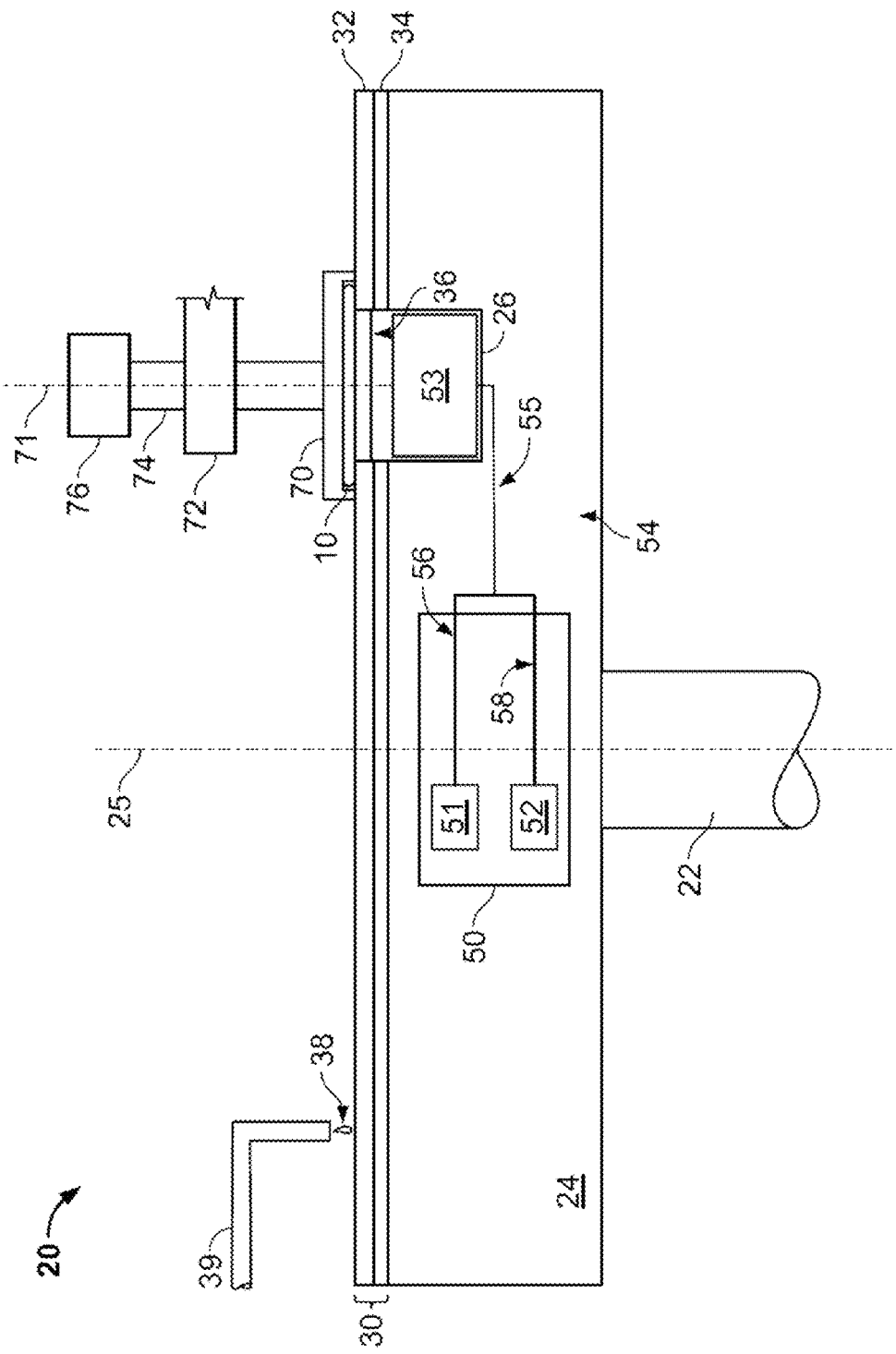
FIG. 1 shows a chemical mechanical polishing apparatus.

FIG. 1 shows a polishing apparatus 20 operable to polish a substrate 10. The polishing apparatus 20 includes a rotatable disk-shaped platen 24, on which a polishing pad 30 is situated. The platen is operable to rotate about axis 25. For example, a motor can turn a drive shaft 22 to rotate the platen 24. The polishing pad 30 can be detachably secured to the platen 24, for example, by a layer of adhesive. When worn, the polishing pad 30 can be detached and replaced. The polishing pad 30 can be a two-layer polishing pad with an outer polishing layer 32 and a softer backing layer 34.

Optical access 36 through the polishing pad is provided by including an aperture (i.e., a hole that runs through the pad) or a solid window. The solid window can be secured to the polishing pad, although in some implementations the solid window can be supported on the platen 24 and project into an aperture in the polishing pad. The polishing pad 30 is usually placed on the platen 24 so that the aperture or window overlies an optical head 53 situated in a recess 26 of the platen 24. The optical head 53 consequently has optical access through the aperture or window to a substrate being polished.

The window can be, for example, a rigid crystalline or glassy material, e.g., quartz or glass, or a softer plastic material, e.g., silicone, polyurethane or a halogenated polymer (e.g., a fluoropolymer), or a combination of the materials mentioned. The window can be transparent to white light. If a top surface of the solid window is a rigid crystalline or glassy material, then the top surface should be sufficiently recessed from the polishing surface to prevent scratching. If the top surface is near and may come into contact with the polishing surface, then the top surface of the window should be a softer plastic material. In some implementations the solid window is secured in the polishing pad and is a polyurethane window, or a window having a combination of quartz and polyurethane. The window can have high transmittance, for example, approximately 80% transmittance, for monochromatic light of a particular color, for example, blue light or red light. The window can be sealed to the polishing pad 30 so that liquid does not leak through an interface of the window and the polishing pad 30.

In one implementation, the window includes a rigid crystalline or glassy material covered with an outer layer of a softer plastic material. The top surface of the softer material can be coplanar with the polishing surface. The bottom surface of the rigid material can be coplanar with or recessed relative to the bottom surface of the polishing pad. In particular, if the polishing pad includes two layers, the solid window can be integrated into the polishing layer, and the bottom layer can have an aperture aligned with the solid window.

A bottom surface of the window can optionally include one or more recesses. A recess can be shaped to accommodate, for example, an end of an optical fiber cable or an end of an eddy current sensor. The recess allows the end of the optical fiber cable or the end of the eddy current sensor to be situated at a distance, from a substrate surface being polished, that is less than a thickness of the window. With an implementation in which the window includes a rigid crystalline portion or glass like portion and the recess is formed in such a portion by machining, the recess is polished so as to remove scratches caused by the machining. Alternatively, a solvent and/or a liquid polymer can be applied to the surfaces of the recess to remove scratches caused by machining. The removal of scratches usually caused by machining reduces scattering and can improve the transmittance of light through the window.

The polishing pad's backing layer 34 can be attached to its outer polishing layer 32, for example, by adhesive. The aperture that provides optical access 36 can be formed in the pad 30, e.g., by cutting or by molding the pad 30 to include the aperture, and the window can be inserted into the aperture and secured to the pad 30, e.g., by an adhesive. Alternatively, a liquid precursor of the window can be dispensed into the aperture in the pad 30 and cured to form the window. Alternatively, a solid transparent element, e.g., the above described crystalline or glass like portion, can be positioned in liquid pad material, and the liquid pad material can be cured to form the pad 30 around the transparent element. In either of the later two cases, a block of pad material can be formed, and a layer of polishing pad with the molded window can be scythed from the block.

The polishing apparatus 20 includes a combined slurry/rinse arm 39. During polishing, the arm 39 is operable to dispense slurry 38 containing a liquid and a pH adjuster. Alternatively, the polishing apparatus includes a slurry port operable to dispense slurry onto polishing pad 30.

The polishing apparatus 20 includes a carrier head 70 operable to hold the substrate 10 against the polishing pad 30. The carrier head 70 is suspended from a support structure 72, for example, a carousel, and is connected by a carrier drive shaft 74 to a carrier head rotation motor 76 so that the carrier head can rotate about an axis 71. In addition, the carrier head 70 can oscillate laterally in a radial slot formed in the support structure 72. In operation, the platen is rotated about its central axis 25, and the carrier head is rotated about its central axis 71 and translated laterally across the top surface of the polishing pad.

The polishing apparatus also includes an optical monitoring system, which can be used to determine a polishing endpoint as discussed below. The optical monitoring system includes a light source 51 and a light detector 52. Light passes from the light source 51, through the optical access 36 in the polishing pad 30, impinges and is reflected from the substrate 10 back through the optical access 36, and travels to the light detector 52.

A bifurcated optical cable 54 can be used to transmit the light from the light source 51 to the optical access 36 and back from the optical access 36 to the light detector 52. The bifurcated optical cable 54 can include a "trunk" 55 and two "branches" 56 and 58.

As mentioned above, the platen 24 includes the recess 26, in which the optical head 53 is situated. The optical head 53 holds one end of the trunk 55 of the bifurcated fiber cable 54, which is configured to convey light to and from a substrate surface being polished. The optical head 53 can include one or more lenses or a window overlying the end of the bifurcated fiber cable 54. Alternatively, the optical head 53 can merely hold the end of the trunk 55 adjacent to the solid window in the polishing pad. The optical head 53 can be removed from the recess 26 as required, for example, to effect preventive or corrective maintenance.

The platen includes a removable in-situ monitoring module 50. The in-situ monitoring module 50 can include one or more of the following: the light source 51, the light detector 52, and circuitry for sending and receiving signals to and from the light source 51 and light detector 52. For example, the output of the detector 52 can be a digital electronic signal that passes through a rotary coupler, e.g., a slip ring, in the drive shaft 22 to the controller for the optical monitoring system. Similarly, the light source can be turned on or off in response to control commands in digital electronic signals that pass from the controller through the rotary coupler to the module 50.

The in-situ monitoring module 50 can also hold the respective ends of the branch portions 56 and 58 of the bifurcated optical fiber 54. The light source is operable to transmit light, which is conveyed through the branch 56 and out the end of the trunk 55 located in the optical head 53, and which impinges on a substrate being polished. Light reflected from the substrate is received at the end of the trunk 55 located in the optical head 53 and conveyed through the branch 58 to the light detector 52.

In one implementation, the bifurcated fiber cable 54 is a bundle of optical fibers. The bundle includes a first group of optical fibers and a second group of optical fibers. An optical fiber in the first group is connected to convey light from the light source 51 to a substrate surface being polished. An optical fiber in the second group is connected to receive light reflecting from the substrate surface being polished and convey the received light to the light detector 52. The optical fibers can be arranged so that the optical fibers in the second group form an X-like shape that is centered on the longitudinal axis of the bifurcated optical fiber 54 (as viewed in a cross section of the bifurcated fiber cable 54). Alternatively, other arrangements can be implemented. For example, the optical fibers in the second group can form V-like shapes that are mirror images of each other. A suitable bifurcated optical fiber is available from Verity Instruments, Inc. of Carrollton, Tex.

There is usually an optimal distance between the polishing pad window and the end of the trunk 55 of bifurcated fiber cable 54 proximate to the polishing pad window. The distance can be empirically determined and is affected by, for example, the reflectivity of the window, the shape of the light beam emitted from the bifurcated fiber cable, and the distance to the substrate being monitored. In one implementation, the bifurcated fiber cable is situated so that the end proximate to the window is as close as possible to the bottom of the window without actually touching the window. With this implementation, the polishing apparatus 20 can include a mechanism, e.g., as part of the optical head 53, that is operable to adjust the distance between the end of the bifurcated fiber cable 54 and the bottom surface of the polishing pad window. Alternatively, the proximate end of the bifurcated fiber cable 54 is embedded in the window.

The light source 51 is operable to emit white light. In one implementation, the white light emitted includes light having wavelengths of 200-800 nanometers. A suitable light source is a xenon lamp or a xenon-mercury lamp.

The light detector 52 can be a spectrometer. A spectrometer is basically an optical instrument for measuring properties of light, for example, intensity, over a portion of the electromagnetic spectrum. A suitable spectrometer is a grating spectrometer. Typical output for a spectrometer is the intensity of the light as a function of wavelength.

Figure 2:
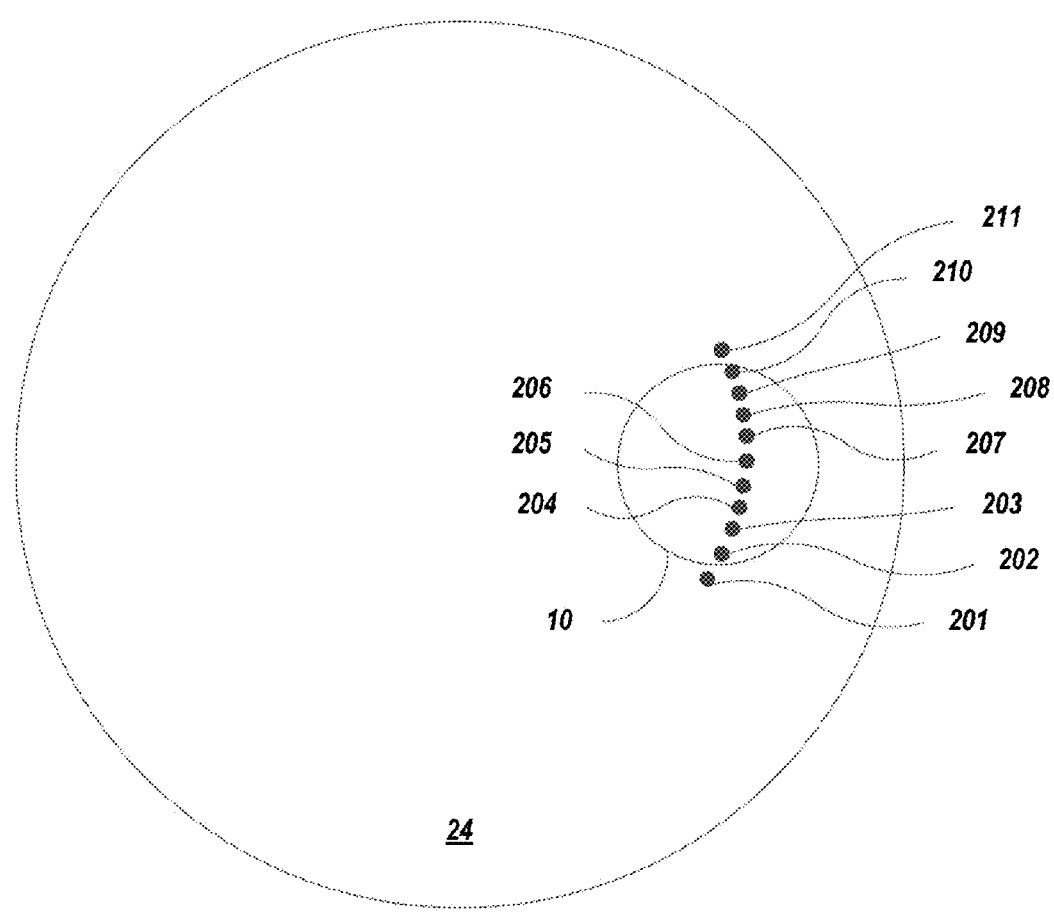
FIG. 2 is an overhead view of a polishing pad and shows locations where in-situ measurements are taken.

The light source 51 and light detector 52 are connected to a computing device operable to control their operation and to receive their signals. The computing device can include a microprocessor situated near the polishing apparatus, e.g., a personal computer. With respect to control, the computing device can, for example, synchronize activation of the light source 51 with the rotation of the platen 24. As shown in FIG. 2, the computer can cause the light source 51 to emit a series of flashes starting just before and ending just after the substrate 10 passes over the in-situ monitoring module 50. Each of points 201-211 represents a location where light from the in-situ monitoring module 50 impinged upon and reflected off of the substrate 10. Alternatively, the computer can cause the light source 51 to emit light continuously starting just before and ending just after the substrate 10 passes over the in-situ monitoring module 50.

The spectra obtained as polishing progresses, e.g., from successive sweeps of the sensor in the platen across the substrate, provide a sequence of spectra. In some implementations, the light source 51 emits a series of flashes of light onto multiple portions of the substrate 10. For example, the light source can emit flashes of light onto a center portion of the substrate 10 and an exterior portion of the substrate 10. Light reflected off of the substrate 10 can be received by the light detector 52 in order to determine multiple sequences of spectra from multiple portions of the substrate 10. Features can be identified in the spectra where each feature is associated with one portion of the substrate 10. The features can be used, for example, in determining an endpoint condition for polishing of the substrate 10. In some implementations, monitoring of multiple portions of the substrate 10 allows for changing the polishing rate on one or more of the portions of the substrate 10.

Figure 3A:
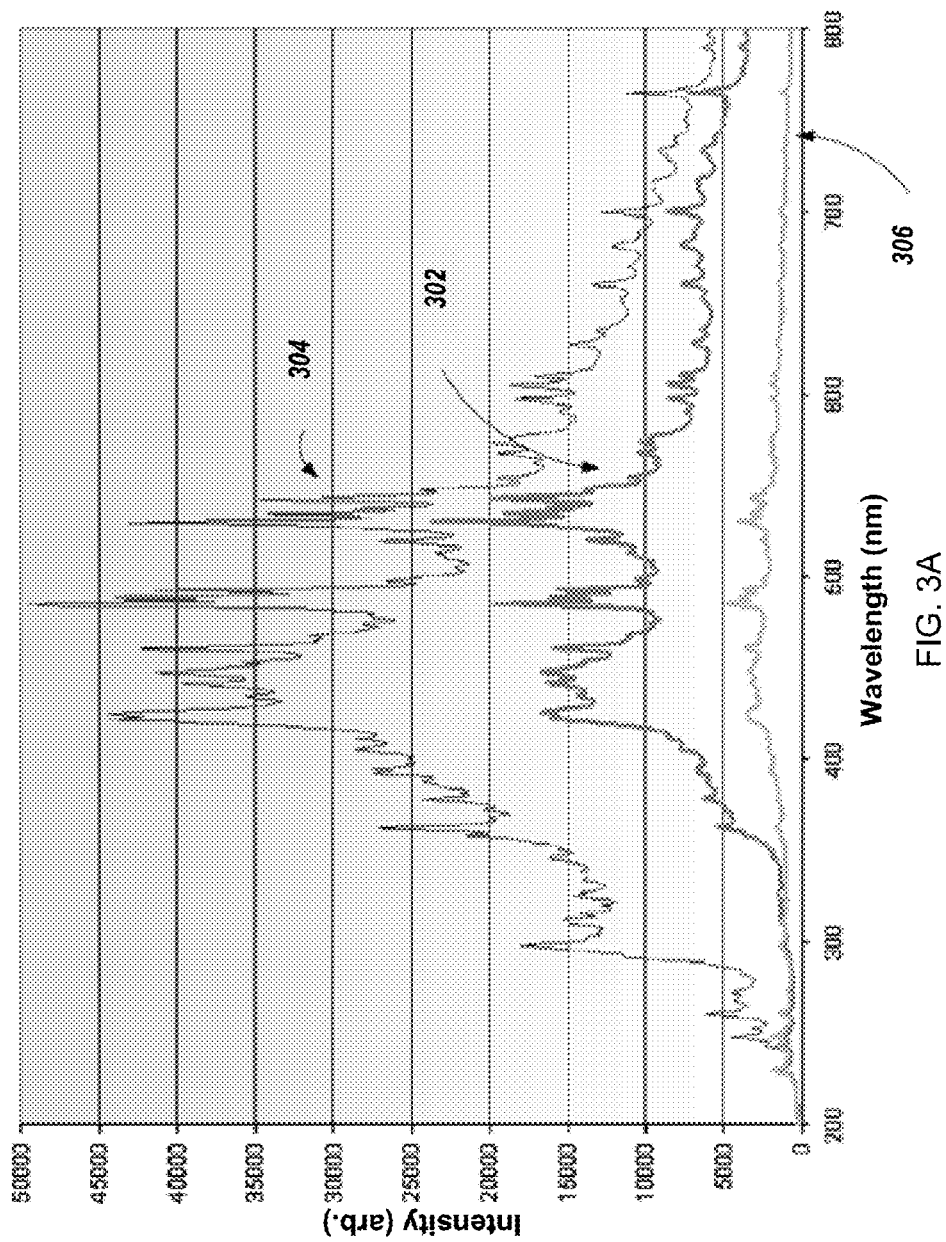
FIG. 3A shows a spectrum obtained from in-situ measurements.

With respect to receiving signals, the computing device can receive, for example, a signal that carries information describing a spectrum of the light received by the light detector 52. FIG. 3A shows examples of a spectrum measured from light that is emitted from a single flash of the light source and that is reflected from the substrate. Spectrum 302 is measured from light reflected from a product substrate. Spectrum 304 is measured from light reflected from a base silicon substrate (which is a wafer that has only a silicon layer). Spectrum 306 is from light received by the optical head 53 when there is no substrate situated over the optical head 53. Under this condition, referred to in the present specification as a dark condition, the received light is typically ambient light.

Figure 3B:
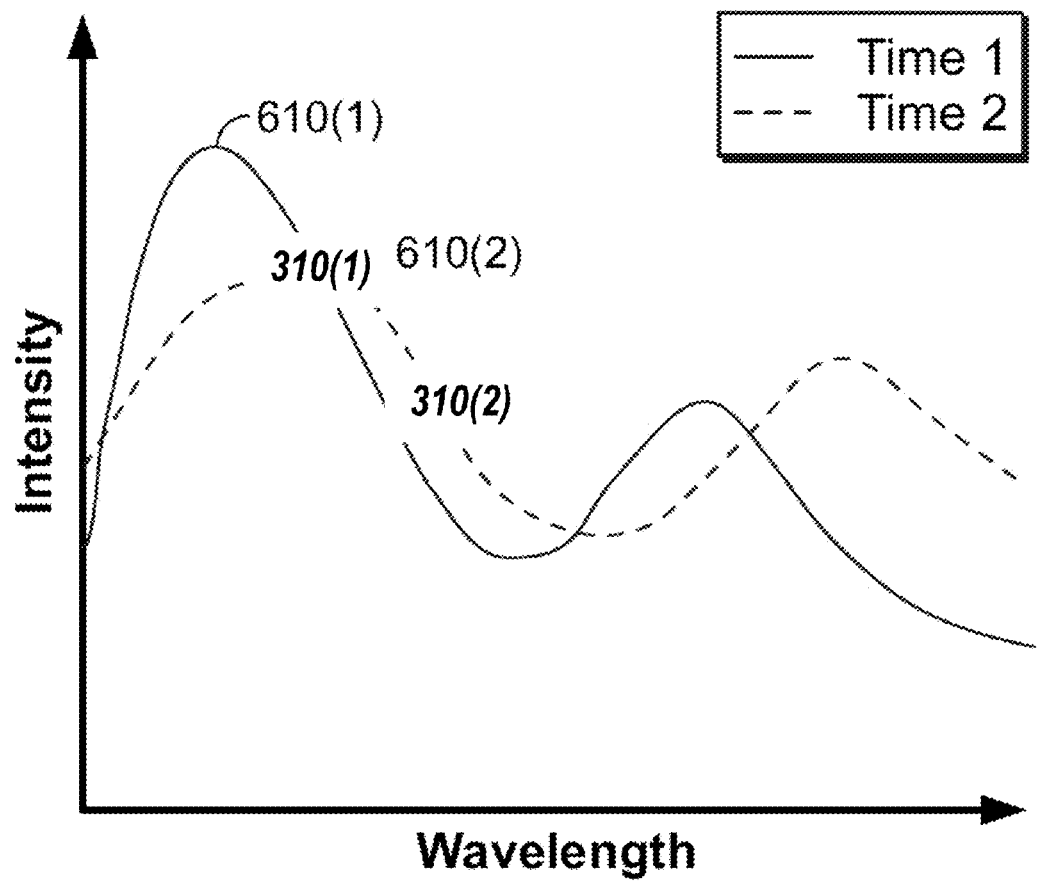
FIG. 3B illustrates the evolution of spectra obtained from in-situ measurements as polishing progresses.

The computing device can process the above-described signal, or a portion thereof, to determine an endpoint of a polishing step. Without being limited to any particular theory, the spectrum of light reflected from the substrate 10 evolves as polishing progresses. FIG. 3B provides an example of the evolution of the spectrum as polishing of a film of interest progresses. The different lines of spectrum represent different times in the polishing. As can be seen, properties of the spectrum of the reflected light change as a thickness of the film changes, and particular spectrums are exhibited by particular thicknesses of the film. When a peak (that is, a local maximum) in the spectrum of reflected light is observed as the polishing of a film progresses, the height of the peak typically changes, and the peak tends to grow wider as material is removed. In addition to widening, the wavelength at which a particular peak is located typically increases as polishing progresses. In some implementations, the wavelength at which a particular peak is located typically decreases as polishing progresses. For example, peak 310(1) illustrates a peak in the spectrum at a certain time during polishing, and peak 310(2) illustrates the same peak at a later time during polishing. Peak 310(2) is located at a longer wavelength and is wider than peak 310(1).

The relative change in the wavelength and/or width of a peak (e.g., the width measured at a fixed distance below the peak or measured at a height halfway between the peak and the nearest valley), the absolute wavelength and/or width of the peak, or both can be used to determine the endpoint for polishing according to an empirical formula. The best peak (or peaks) to use when determining the endpoint varies depending on what materials are being polished and the pattern of those materials.

In some implementations, a change in peak wavelength can be used to determine endpoint. For example, when the difference between the starting wavelength of a peak and the current wavelength of the peak reaches a target difference, the polishing apparatus 20 can stop polishing the substrate 10. Alternatively, features other than peaks can be used to determine a difference in the wavelength of light reflected from the substrate 10. For example, the wavelength of a valley, an inflection point, or an x- or y-axis intercept can be monitored by the light detector 52, and when the wavelength has changed by a predetermined amount, the polishing apparatus 20 can stop polishing the substrate 10.

In some implementations, the characteristic that is monitored is the width or the intensity of the feature instead of, or in addition to the wavelength. Features can shift on the order of 40 nm to 120 nm, although other shifts are possible, For example, the upper limit could be much greater, especially in the case of a dielectric polish.

FIG. 4A provides an example of a measured spectrum 400a of light reflected from the substrate 10. The optical monitoring system can pass the spectrum 400a through a high-pass filter in order to reduce the overall slope of the spectrum, resulting in a spectrum 400b shown in FIG. 4B. During processing of multiple substrates in a batch, for example, large spectra differences can exist among wafers. A high-pass filter can be used to normalize the spectra in order to reduce spectra variations across substrates in the same batch. An exemplary high-pass filter can have a cutoff of 0.005 Hz and a filter order of 4. The high-pass filter is not only used to help filter out sensitivity to underlying variation, but also to "flatten" out the legitimate signal to make feature tracking easier.

Figures 5A, 5B:
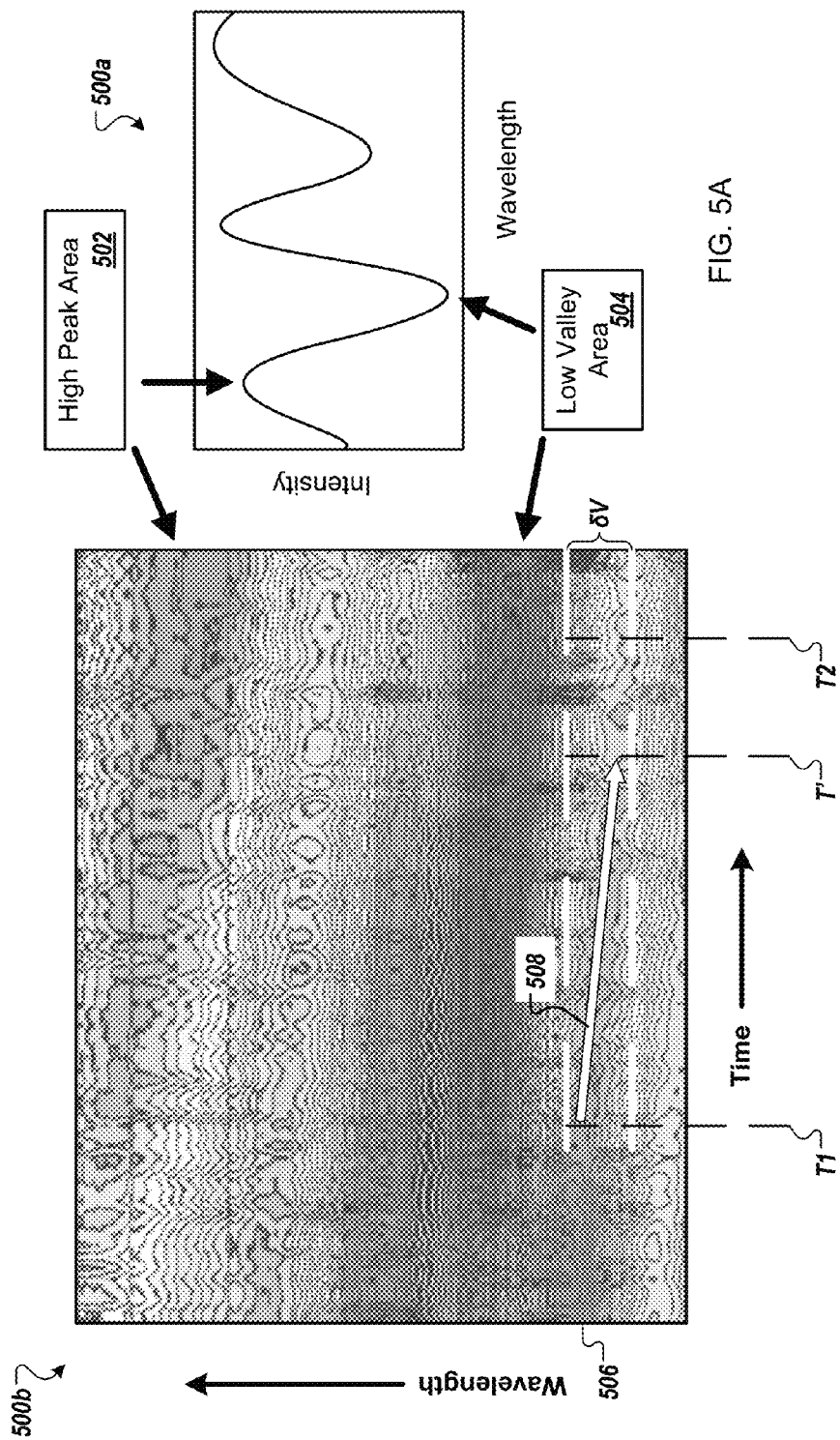
FIG. 5A shows a spectrum of light reflected from a substrate.
FIG. 5B shows a contour plot of spectra obtained from in-situ measurements of light reflected from a substrate.

In order for a user to select which feature of the endpoint to track to determine the endpoint, a contour plot can be generated and displayed to the user. FIG. 5B provides an example of a contour plot 500b generated from multiple spectra measurements of light reflected off of the substrate 10 during polishing, and FIG. 5A provides an example of a measured spectrum 500a from a particular moment in the contour plot 500b. The contour plot 500b includes features, such as a peak area 502 and a valley area 504 which result from associated peaks 502 and valleys 504 on the spectrum 500a. As time progresses, the substrate 10 is polished and the light reflected from the substrate changes, as shown by changes to the spectral features in the contour plot 500b.

In order to generate the contour plot 500b, a test substrate can be polished, and the light reflected from the test substrate can be measured by the light detector 52 during polishing to generate a sequence of spectra of light reflected from the substrate 10. The sequence of spectra can be stored, e.g., in a computer system, which optionally can be part of the optical monitoring system. Polishing of the set up substrate can start at time T1 and continue past an estimated endpoint time.

When polishing of the test substrate is complete, the computer renders the contour plot 500b for presentation to an operator of the polishing apparatus 20, e.g., on a computer monitor. In some implementations, the computer color-codes the contour-plot, e.g., by assigning red to the higher intensity values in the spectra, blue to the lower intensity values in the spectra, and intermediate colors (orange through green) to the intermediate intensity values in the spectra. In other implementations, the computer creates a grayscale contour plot by assigning the darkest shade of gray to lower intensity values in the spectra, and the lightest shade of gray to higher intensity values in the spectra, with intermediate shades for the intermediate intensity values in the spectra. Alternatively, the computer can generate a 3-D contour plot with the largest z value for higher intensity values in the spectra, and the smallest z value for lower intensity values in the spectra, with intermediate z values for the intermediate values in the spectra. A 3-D contour plot can be, for example, displayed in color, grayscale, or black and white. In some implementations, the operator of the polishing apparatus 20 can interact with a 3-D contour plot in order to view different features of the spectra.

The contour plot 500b of the reflected light generated from monitoring of the test substrate during polishing can contain, for example, spectral features such as peaks, valleys, spectral zero-crossing points, and inflection points. The features can have characteristics such as wavelengths, widths, and/or intensities. As shown by the contour plot 500b, as the polishing pad 30 removes material from the top surface of the set up substrate, the light reflected off of the set up substrate can change over time, so feature characteristics change over time.

Prior to polishing of the device substrates, an operator of the polishing apparatus 20 can view the contour plot 500b and select a feature characteristic to track during processing of a batch of substrates that have similar die features as the set up substrate. For example, the wavelength of a peak 506 can be selected for tracking by the operator of the polishing apparatus 20. A potential advantage of the contour plot 500b, particularly a color-coded or 3-D contour plot, is that such a graphical display makes the selection of a pertinent feature by the user easier, since the features, e.g., features with characteristics that change linearly with time, are easily visually distinguishable.

In order to select an endpoint criterion, the characteristic of the selected feature can be calculated by linear interpolation based on the pre-polish thickness and the post-polish thickness of the test substrate. For example, thicknesses D1 and D2 of the layer on the test substrate can be measured at pre-polish (e.g., the thickness of the test substrate before time T1 when polishing starts) and at post-polish (e.g., the thickness of the test substrate after time T2 when polishing ends) respectively, and the values of the characteristic can be measured at the time T' at which the target thickness D' is achieved. T' can be calculated from $T'=T1+(T2-T1)*(D2-D')/(D2-D1)$, and the value V' of the characteristic can be determined from the spectrum measured at time T'. A target difference, $\delta V$, for the characteristic of the selected feature, such as a specific change in the wavelength of the peak 506, can be determined from V'−V1, where V1 is the initial characteristic value (at the time T1). Thus, the target difference $\delta V$ can be the change from the initial value of the characteristic V1 before polishing at time T1 to the value of the characteristic V' at time T' when polishing is expected to be completed. An operator of the polishing apparatus 20 can enter a target difference 604 (e.g., $\delta V$) for the feature characteristic to change into a computer associated with the polishing apparatus 20.

In order to determine the value of V' which in turn determines the value of points 602, a robust line fitting can be used to fit a line 508 to the measured data. The value of line 508 at time T' minus the value of line 508 at T1 can be used to determine points 602.

The feature, such as the spectral peak 506, can be selected based on correlation between the target difference of the feature characteristic and the amount of material removed from the set up substrate during polishing. The operator of the polishing apparatus 20 can select a different feature and/or feature characteristic in order to find a feature characteristic with a good correlation between the target difference of the characteristic and the amount of material removed from the set up substrate.

In other implementations, endpoint determination logic determines the spectral feature to track and the endpoint criterion.

Figure 6A:
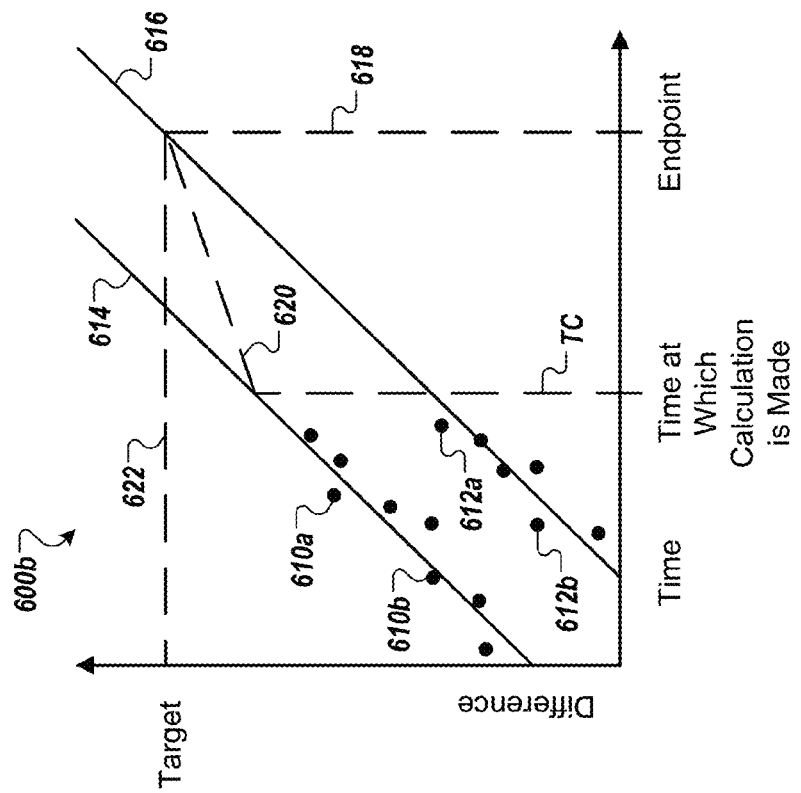
FIG. 6A shows an example graph of polishing progress, measured in characteristic difference versus time.

Turning now to the polishing of a device substrate, FIG. 6A is an example graph 600a of difference values 602a-d of a tracked feature characteristic during polishing of a device substrate 10. The substrate 10 can be part of a batch of substrates being polished where an operator of the polishing apparatus 20 selected a feature characteristic, such as the wavelength of a peak or a valley, to track from the contour plot 500b of a set up substrate.

As the substrate 10 is polished, the light detector 52 measures spectra of light reflected from the substrate 10. The endpoint determination logic uses the spectra of light to determine a sequence of values for the feature characteristic. The values of the selected feature characteristic can change as material is removed from the surface of the substrate 10. The difference between the sequence of values of the feature characteristic and the initial value of the feature characteristic V1 is used to determine the difference values 602a-d.

As the substrate 10 is polished the endpoint determination logic can determine the current value of the feature characteristic being tracked. In some implementations, when the current value of the feature has changed from the initial value by the target difference 604, endpoint can be called. In some implementations, a line 606 is fit to the difference values 602a-d, e.g., using a robust line fit. A function of the line 606 can be determined based on the difference values 602a-d in order to predict polishing endpoint time. In some implementations, the function is a linear function of time versus characteristic difference. The function of the line 606, e.g., the slope and intersects, can change during polishing of the substrate 10 as new difference values are calculated. In some implementations, the time at which the line 606 reaches the target difference 604 provides an estimated endpoint time 608. As the function of the line 606 changes to accommodate new difference values, the estimated endpoint time 608 can change.

In some implementations, the function of the line 606 is used to determine the amount of material removed from the substrate 10 and a change in the current value determined by the function is used to determine when the target difference has been reached and endpoint needs to be called. Line 606 tracks amount of material removed. Alternatively, when removing a specific thickness of material from the substrate 10, a change in the current value determined by the function can be used to determine the amount of material removed from the top surface of the substrate 10 and when to call endpoint. For example, an operator can set the target difference to be a change in wavelength of the selected feature by 50 nanometers. For example, the change in the wavelength of a selected peak can be used to determine how much material has been removed from the top layer of the substrate 10 and when to call endpoint.

At time T1, before polishing of the substrate 10, the characteristic value difference of the selected feature is 0. As the polishing pad 30 begins to polish the substrate 10 the characteristic values of the identified feature can change as material is polished off of the top surface of the substrate 10. For example, during polishing the wavelength of the selected feature characteristic can move to a higher or lower wavelength. Excluding noise effects, the wavelength, and thus the difference in wavelength, of the feature tends to change monotonically, and often linearly. At time T' endpoint determination logic determines that the identified feature characteristic has changed by the target difference, δV, and endpoint can be called. For example, when the wavelength of the feature has changed by a target difference of 50 nanometers, endpoint is called and the polishing pad 30 stops polishing the substrate 10.

When processing a batch of substrates the optical monitoring system 50 can, for example, track the same spectral feature across all of the substrates. The spectral feature can be associated with the same die feature on the substrates. The starting wavelength of the spectral feature can change from substrate to substrate across the batch based on underlying variations of the substrates. In some implementations, in order to minimize variability across multiple substrates, endpoint determination logic can call endpoint when the selected feature characteristic value or a function fit to values of the feature characteristic changes by an endpoint metric, EM, instead of the target difference. The endpoint determination logic can use an expected initial value, EIV, determined from a set up substrate. At time T1 when the feature characteristic being tracked on the substrate 10 is identified, the endpoint determination logic determines the actual initial value, AIV, for a substrate being processed. The endpoint determination logic can use an initial value weight, IVW, to reduce the influence of the actual initial value on the endpoint determination while taking into consideration variations in substrates across a batch. Substrate variation can include, for example, substrate thickness or the thickness of underlying structures. The initial value weight can correlate to the substrate variations in order to increase uniformity between substrate to substrate processing. The endpoint metric can be, for example, determined by multiplying the initial value weight by the difference between the actual initial value and the expected initial value and adding the target difference, e.g., $EM = IVW*(AIV-EIV)+\delta V$.

In some implementations, a weighted combination is used to determine endpoint. For example, the endpoint determination logic can calculate an initial value of the characteristic from the function and a current value of the characteristic from the function, and a first difference between the initial value and the current value. The endpoint determination logic can calculate a second difference between the initial value and a target value and generate a weighted combination of the first difference and the second difference.

Figure 6B:
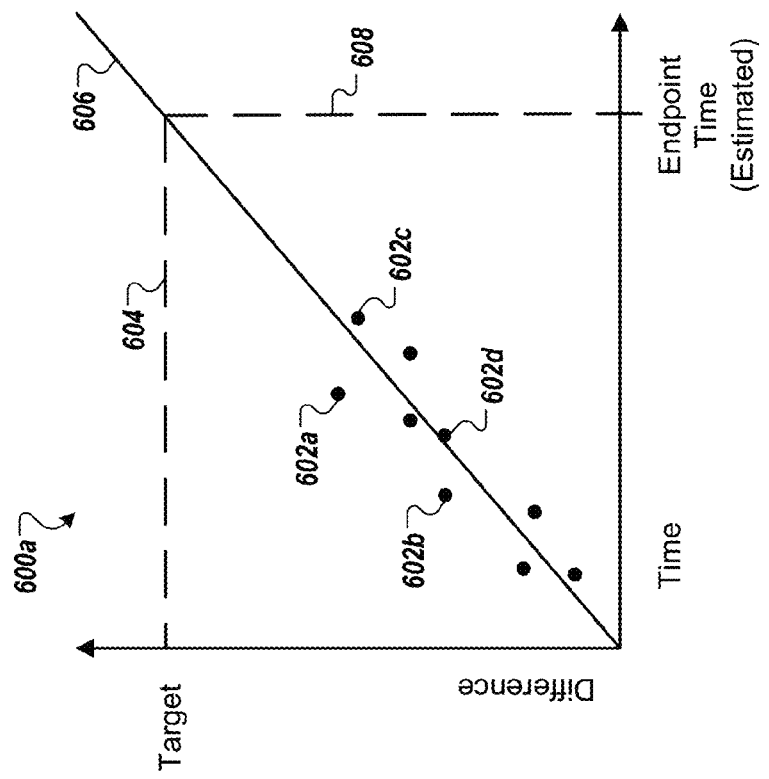
FIG. 6B shows an example graph of polishing progress, measured in characteristic difference versus time in which characteristics of two different features are measured in order to adjust the polishing rate of a substrate.

FIG. 6B is an example graph 600b of characteristic measurement differences versus time taken at two portions of the substrate 10. For example, the optical monitoring system 50 can track one feature located toward an edge portion of the substrate 10 and another feature located toward a center portion of the substrate 10 in order to determine how much material has been removed from the substrate 10. When testing a set up substrate, an operator of the polishing apparatus 20 can, for example, identify two features to track that correspond to different portions of the set up substrate. In some implementations, the spectral features correspond with the same type of die features on the set up substrate. In other implementations, the spectral features are associated with different types of die features on the set up substrate. As the substrate 10 is being polished, the light detector 52 can measure a sequence of spectra of reflected light from the two portions of the substrate 10 that correspond with the selected features of the set up substrate. A sequence of values associated with characteristics of the two features can be determined by endpoint determination logic. A sequence of first difference values 610a-b can be calculated for a feature characteristic in a first portion of the substrate 10 by subtracting the initial characteristic value from the current characteristic value as polishing time progresses. A sequence of second difference values 612a-b can similarly be calculated for a feature characteristic in a second portion of the substrate 10.

A first line 614 can be fit to the first difference values 610a-b and a second line 616 can be fit to the second difference values 612a-b. The first line 614 and the second line 616 can be determined by a first function and a second function, respectively, in order to determine an estimated polishing endpoint time 618 or an adjustment to the polishing rate 620 of the substrate 10.

During polishing, an endpoint calculation based on a target difference 622 is made at time TC with the first function for the first portion of the substrate 10 and with the second function for the second portion of the substrate. If the estimated endpoint time for the first portion of the substrate and the second portion of the substrate differ (e.g., the first portion will reach the target thickness before the second portion) an adjustment to the polishing rate 620 can be made so that the first function and the second function will have the same endpoint time 618. In some implementations, the polishing rates of both the first portion and the second portion of the substrate are adjusted so that endpoint is reached at both portions simultaneously. Alternatively, the polishing rate of either the first portion or the second portion can be adjusted.

The polishing rates can be adjusted by, for example, increasing or decreasing the pressure in a corresponding region of the carrier head 70. The change in polishing rate can be assumed to be directly proportional to the change in pressure, e.g., a simple Prestonian model. For example, when a the first region of the substrate 10 is projected to reach the target thickness at a time TA, and the system has established a target time TT, the carrier head pressure in the corresponding region before time T3 can be multiplied by TT/TA to provide the carrier head pressure after time T3. Additionally, a control model for polishing the substrates can be developed that takes into account the influences of platen or head rotational speed, second order effects of different head pressure combinations, the polishing temperature, slurry flow, or other parameters that affect the polishing rate. At a subsequent time during the polishing process, the rates can again be adjusted, if appropriate.

In some implementations, a computing device uses a wavelength range in order to easily identify a selected spectral feature in a measured spectrum of light reflected from the device substrate 10. The computing device searches the wavelength range for the selected spectral feature in order to distinguish the selected spectral feature from other spectral features that are similar to the selected spectral feature in the measured spectrum, e.g., in intensity, width, or wavelength.

Figure 7A:
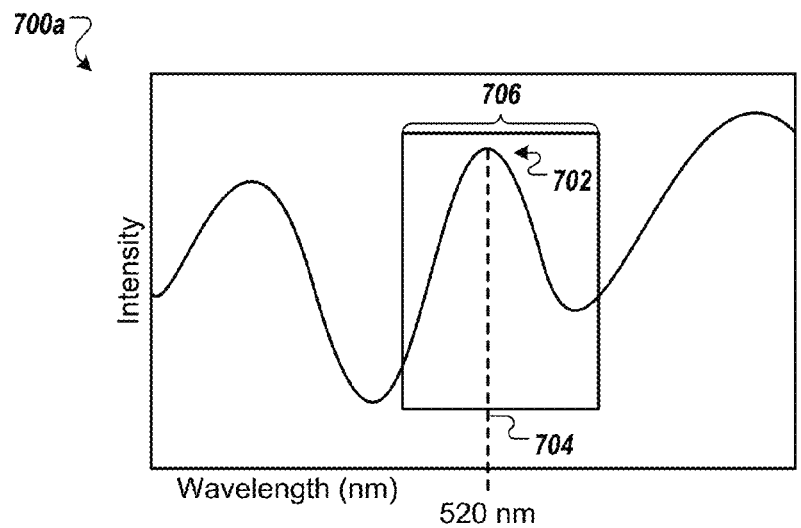
FIG. 7A shows another spectrum of light obtained from in-situ measurements.

FIG. 7A shows an example of a spectrum 700a measured from light received by the light detector 52. The spectrum 700a includes a selected spectral feature 702, e.g., a spectral peak. The selected spectral feature 702 can be selected by endpoint determination logic for tracking during CMP of the substrate 10. A characteristic 704 (e.g., the wavelength) of the selected spectral feature 702 can be identified by the endpoint determination logic. When the characteristic 704 has changed by a target difference, the endpoint determination logic calls endpoint.

In some implementations, the endpoint determination logic determines a wavelength range 706 over which to search for the selected spectral feature 702. The wavelength range 706 can have a width of between about 50 and about 200 nanometers. In some implementations, the wavelength range 706 is predetermined, e.g., specified by an operator, e.g., by receiving user input selecting the wavelength range, or specified as a process parameter for a batch of substrates, by retrieving the wavelength range from a memory associating the wavelength range with the batch of substrates. In some implementations, the wavelength range 706 is based on historical data, e.g., the average or maximum distance between consecutive spectrum measurements. In some implementations, the wavelength range 706 is based on information about a test substrate, e.g., twice the target difference δV.

Figure 7B:
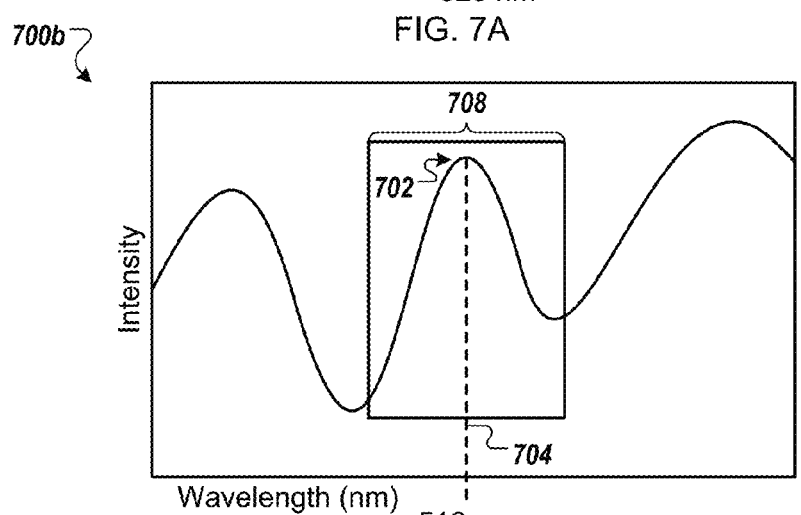
FIG. 7B shows a spectrum of light obtained after the spectrum of FIG. 7A.

FIG. 7B is an example of a spectrum 700b measured from light received by the light detector 52. For example, the spectrum 700b is measured during the rotation of the platen 24 directly after the spectrum 700a was taken. In some implementations, the endpoint determination logic determines the value of the characteristic 704 in the previous spectrum 700a (e.g., 520 nm) and adjusts the wavelength range 706 so that the center of a wavelength range 708 is positioned closer to the characteristic 704.

In some implementations, the endpoint determination logic uses the function of the line 606 to determine an expected current value of the characteristic 704. For example, the endpoint determination logic can use the current polishing time to determine the expected difference and determine the expected current value of the characteristic 704 by adding the expected difference to the initial value V1 of the characteristic 704. The endpoint determination logic can center the wavelength range 708 on the expected current value of the characteristic 704.

Figure 7C:
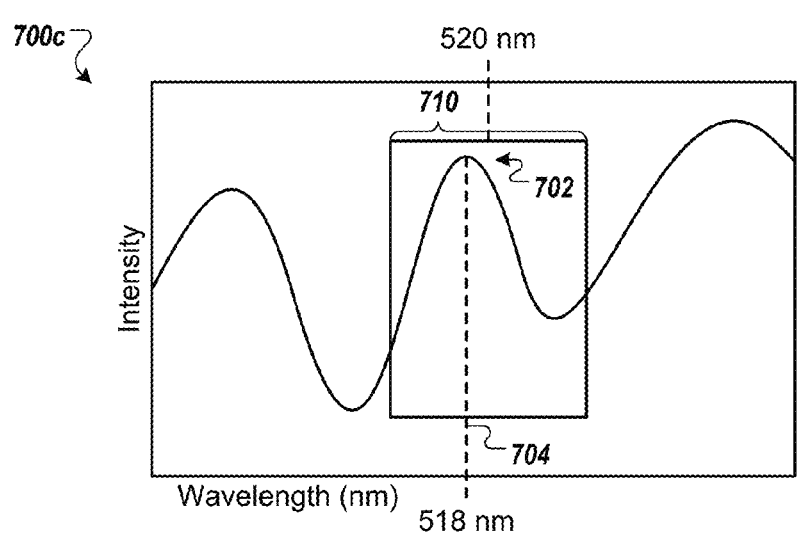
FIG. 7C shows another spectrum of light obtained after the spectrum of FIG. 7A.

FIG. 7C is another example of a spectrum 700c measured from light received by the light detector 52. For example, the spectrum 700c is measured during the rotation of the platen 24 directly after the spectrum 700a was taken. In some implementations, the endpoint determination logic uses the previous value of the characteristic 704 for the center of a wavelength range 710.

For example, the endpoint determination logic determines the average variance between values of the characteristic 704 determined during two consecutive passes of the optical head 53 below the substrate 10. The endpoint determination logic can set the width of the wavelength range 710 to twice the average variance. In some implementations, the endpoint determination logic uses the standard deviation of the variance between values of the characteristic 704 in determining the width of the wavelength range 710.

In some implementations, the width of the wavelength range 706 is the same for all spectra measurements. For example, the width of the wavelength range 706, the wavelength range 708, and the wavelength range 710 are the same. In some implementations, the widths of the wavelength ranges are different. For example, when the characteristic 704 is estimated to change by 2 nanometers from the previous measurement of the characteristic, the width of the wavelength range 708 is 60 nanometers. When the characteristic 704 is estimated to change by 5 nanometers from the previous measurement of the characteristic, the width of the wavelength range 708 is 80 nanometers, a greater wavelength range than the range for a smaller change in the characteristic.

In some implementations, the wavelength range 706 is the same for all spectra measurements during polishing of the substrate 10. For example, the wavelength range 706 is 475 nanometers to 555 nanometers and the endpoint determination logic searches for the selected spectral feature 702 in the wavelengths between 475 nanometers and 555 nanometers for all spectra measurements taken during polishing of the substrate 10, although other wavelength ranges are possible. The wavelength range 706 can be selected by user input as a subset of the full spectral range measured by the in-situ monitoring system.

In some implementations, the endpoint determination logic searches for the selected spectral feature 702 in a modified wavelength range in some of the spectra measurements and in a wavelength range used for a previous spectrum in remainder of the spectra. For example, the endpoint determination logic searches for the selected spectral feature 702 in the wavelength range 706 for a spectrum measured during a first rotation of the platen 24 and the wavelength range 708 for a spectrum measured during a consecutive rotation of the platen 24, where both measurements were taken in a first area of the substrate 10. Continuing the example, the endpoint determination logic searches for another selected spectral feature in the wavelength range 710 for two spectra measured during the same platen rotations, where both measurements were taken in a second area of the substrate 10 that is different from the first area.

In some implementations, the selected spectral feature 702 is a spectral valley or a spectral zero-crossing point. In some implementations, the characteristic 704 is an intensity or a width of a peak or valley (e.g., the width measured at a fixed distance below the peak or measured at a height halfway between the peak and the nearest valley).

Figures 8, 9:
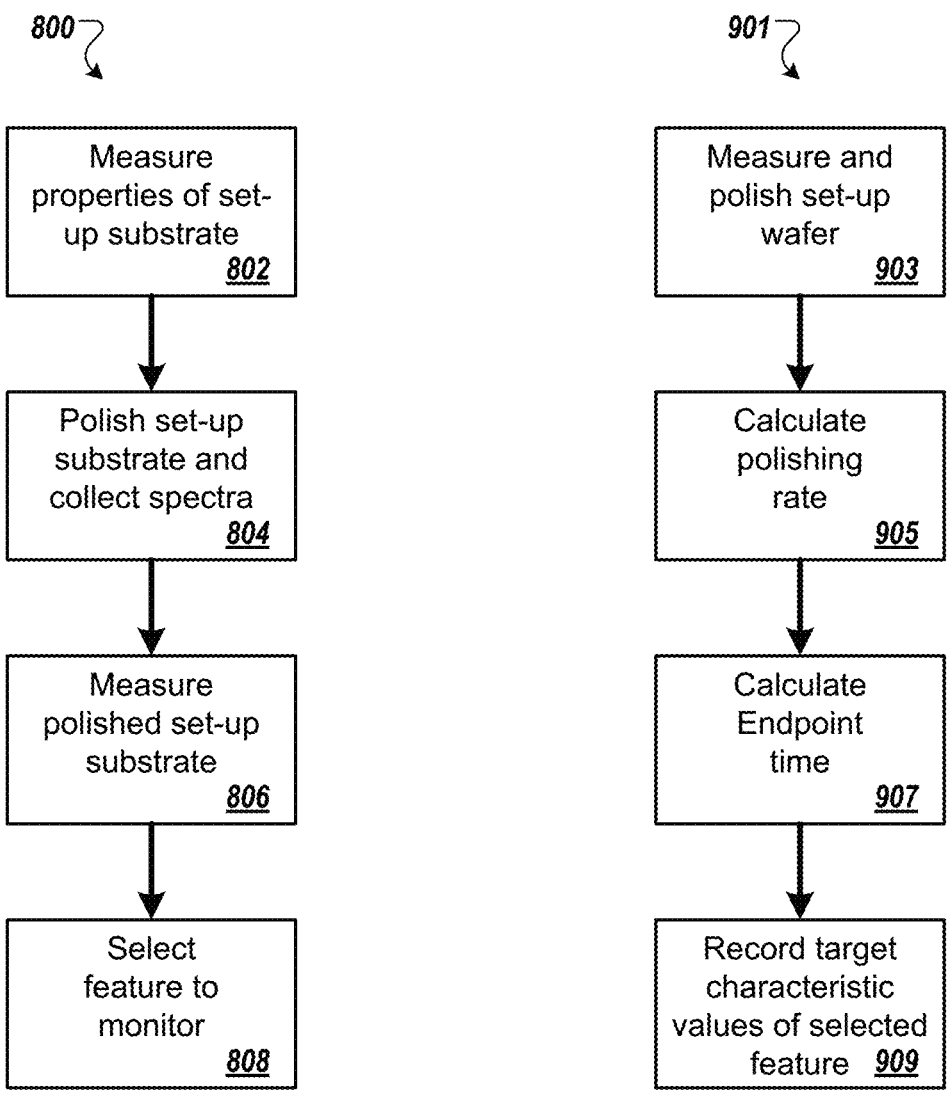
FIG. 8 shows a method for selecting a peak to monitor.
FIG. 9 shows a method for obtaining target parameters for the selected peak.

FIG. 8 shows a method 800 for selecting a target difference δV to use when determining the endpoint for the polishing process. Properties of a substrate with the same pattern as the product substrate are measured (step 802). The substrate which is measured is referred to in the instant specification as a "set-up" substrate. The set-up substrate can simply be a substrate which is similar to or the same as the product substrate, or the set-up substrate can be one substrate from a batch of product substrates. The properties that are measured can include a pre-polished thickness of a film of interest at a particular location of interest on the substrate. Typically, the thicknesses at multiple locations are measured. The locations are usually selected so that a same type of die feature is measured for each location. Measurement can be performed at a metrology station. The in-situ optical monitoring system can measure a spectrum of light reflected off of the substrate before polishing.

The set-up substrate is polished in accordance with a polishing step of interest and the spectra obtained during polishing are collected (step 804). Polishing and spectral collection can be performed at the above described-polishing apparatus. The spectra are collected by the in-situ monitoring system during polishing. The substrate is over-polished, i.e., polished past an estimated endpoint, so that the spectrum of the light that is reflected from the substrate when the target thickness is achieved can be obtained.

Properties of the overpolished substrate are measured (step 806). The properties include post-polished thicknesses of the film of interest at the particular location or locations used for the pre-polish measurement.

The measured thicknesses and the collected spectra are used to select, by examining the collected spectra, a particular feature, such as a peak or a valley, to monitor during polishing (step 808). The feature can be selected by an operator of the polishing apparatus or the selection of the feature can be automated (e.g., based on conventional peak-finding algorithms and an empirical peak-selection formula). For example, the operator of the polishing apparatus 20 can be presented with the contour plot 500b and the operator can select a feature to track from the contour plot 500b as described above with reference to FIG. 5B. If a particular region of the spectrum is expected to contain a feature that is desirable to monitor during polishing (e.g., due to past experience or calculations of feature behavior based on theory), only features in that region need be considered. A feature is typically selected that exhibits a correlation between the amount of material removed from the top of the set-up substrate as the substrate is polished.

Linear interpolation can be performed using the measured pre-polish film thickness and post-polish substrate thickness to determine an approximate time that the target film thickness was achieved. The approximate time can be compared to the spectra contour plot in order to determine the endpoint value of the selected feature characteristic. The difference between the endpoint value and the initial value of the feature characteristic can be used as a target difference. In some implementations, a function is fit to the values of the feature characteristic in order to normalize the values of the feature characteristic. The difference between the endpoint value of the function and the initial value of the function can be used as the target difference. The same feature is monitored during the polishing of the rest of the batch of substrates.

Optionally, the spectra are processed to enhance accuracy and/or precision. The spectra can be processed, for example: to normalize them to a common reference, to average them, and/or to filter noise from them. In one implementation, a low-pass filter is applied to the spectra to reduce or eliminate abrupt spikes.

The spectral feature to monitor typically is empirically selected for particular endpoint determination logic so that the target thickness is achieved when the computer device calls an endpoint by applying the particular feature-based endpoint logic. The endpoint determination logic uses the target difference in feature characteristic to determine when an endpoint should be called. The change in characteristic can be measured relative to the initial characteristic value of the feature when polishing begins. Alternatively, the endpoint can be called relative to an expected initial value, EIV, and an actual initial value, AIV, in addition to the target difference, δV. The endpoint logic can multiply the difference between the actual initial value and the expected initial value by a start value weight, SVW, in order to compensate for underlying variations from substrate to substrate. For example, the endpoint determination logic can end polishing when an endpoint metric, EM=SVW*(AIV−EIV)+δV.

In some implementations, a weighted combination is used to determine endpoint. For example, the endpoint determination logic can calculate an initial value of the characteristic from the function and a current value of the characteristic from the function, and a first difference between the initial value and the current value. The endpoint determination logic can calculate a second difference between the initial value and a target value and generate a weighted combination of the first difference and the second difference. Endpoint can be called with the weighted value reaches a target value. The endpoint determination logic can determine when an endpoint should be called by comparing the monitored difference (or differences) to a target difference of the characteristic. If the monitored difference matches or is beyond the target difference, an endpoint is called. In one implementation the monitored difference must match or exceed the target difference for some period of time (e.g., two revolutions of the platen) before an endpoint is called.

FIG. 9 shows a method 901 for choosing target values of characteristics associated with the selected spectral feature for a particular target thickness and particular endpoint determination logic. A set-up substrate is measured and polished as described above in steps 802-806 (step 903). In particular, spectra are collected and the time at which each collected spectrum is measured is stored.

A polishing rate of the polishing apparatus for the particular set-up substrate is calculated (step 905). The average polishing rate PR can be calculated by using the pre- and post-polished thicknesses D1, D2, and the actual polish time, PT, e.g., PR=(D2−D1)/PT.

An endpoint time is calculated for the particular set-up substrate (step 907) to provide a calibration point to determine target values of the characteristics of the selected feature, as discussed below. The endpoint time can be calculated based on the calculated polish rate PR, the pre-polish starting thickness of the film of interest, ST, and the target thickness of the film of interest, TT. The endpoint time can be calculated as a simple linear interpolation, assuming that the polishing rate is constant through the polishing process, e.g., ET=(ST−TT)/PR.

Optionally, the calculated endpoint time can be evaluated by polishing another substrate of the batch of patterned substrates, stopping polishing at the calculated endpoint time, and measuring the thickness of the film of interest. If the thickness is within a satisfactory range of the target thickness, then the calculated endpoint time is satisfactory. Otherwise, the calculated endpoint time can be re-calculated.

Target characteristic values for the selected feature are recorded from the spectrum collected from the set-up substrate at the calculated endpoint time (step 909). If the parameters of interest involve a change in the selected feature's location or width, that information can be determined by examining the spectra collected during the period of time that preceded the calculated endpoint time. The difference between the initial values and the target values of the characteristics are recorded as the target differences for the feature. In some implementations, a single target difference is recorded.

Figure 10:
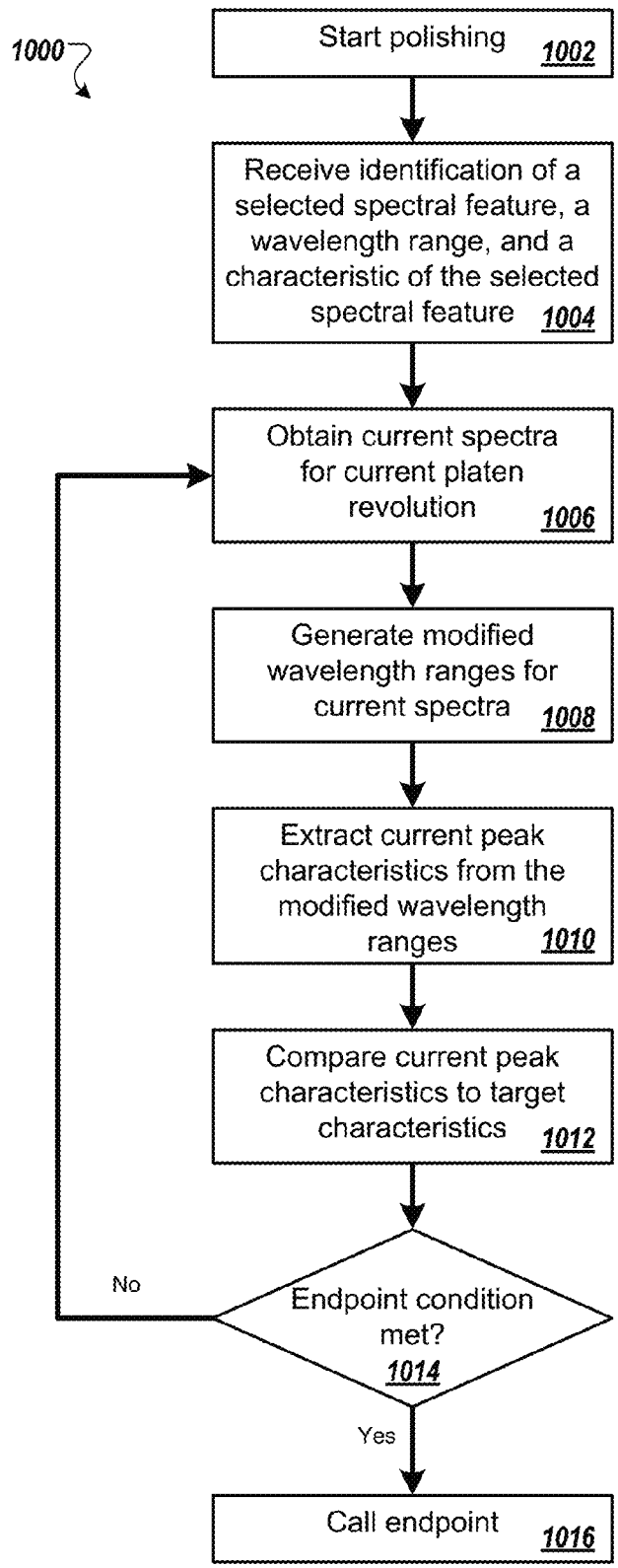
FIG. 10 shows a method for endpoint determination.

FIG. 10 shows a method 1000 for using peak-based endpoint determination logic to determine an endpoint of a polishing step. Another substrate of the batch of patterned substrates is polished using the above-described polishing apparatus (step 1002).

An identification of a selected spectral feature, a wavelength range, and a characteristic of the selected spectral feature are received (step 1004). For example, the endpoint determination logic receives the identification from a computer with processing parameters for the substrate. In some implementations, the processing parameters are based on information determined during processing of a set-up substrate.

The substrate is initially polished, light reflecting from the substrate is measured to create a spectrum, and a characteristic value of the selected spectral feature is determined in the wavelength range of the measured spectrum. At each revolution of the platen, the following steps are performed.

One or more spectra of light reflecting off a substrate surface being polished are measured to obtain one or more current spectra for a current platen revolution (step 1006). The one or more spectra measured for the current platen revolution are optionally processed to enhance accuracy and/or precision as described above in reference to FIG. 8. If only one spectrum is measured, then the one spectrum is used as the current spectrum. If more than one current spectrum is measured for a platen revolution, then they are grouped, averaged within each group, and the averages are designated to be current spectra. The spectra can be grouped by radial distance from the center of the substrate.

By way of example, a first current spectrum can be obtained from spectra measured at points 202 and 210 (FIG. 2), a second current spectrum can be obtained from spectra measured at points 203 and 209, a third current spectra can be obtained from spectra measured at points 204 and 208, and so on. The characteristic values of the selected spectral peak can be determined for each current spectrum, and polishing can be monitored separately in each region of the substrate. Alternatively, worst-case values for the characteristics of the selected spectral peak can be determined from the current spectra and used by the endpoint determination logic.

During each revolution of the platen, an additional spectrum or spectra are added to the sequence of spectra for the current substrate. As polishing progresses at least some of the spectra in the sequence differ due to material being removed from the substrate during polishing.

Modified wavelength ranges for the current spectra are generated (step 1008) as described above with reference to FIGS. 7A-C. For example, the endpoint logic determines modified wavelength ranges for the current spectra based on previous characteristic values. The modified wavelength ranges can be centered on the previous characteristic values.

In some implementations, the modified wavelength ranges are determined based on expected characteristic values, e.g., the center of the wavelength ranges coincide with the expected characteristic values.

In some implementations, some of the wavelength ranges for the current spectra are determined using different methods. For example, a wavelength range for a spectrum measured from light reflected in an edge area of the substrate is determined by centering the wavelength range on the characteristic value from the previous spectrum measured in the same edge area of the substrate. Continuing the example, a wavelength range for a spectrum measured from light reflected in a center area of the substrate is determined by centering the wavelength range on the expected characteristic value for the center area.

In some implementations, the widths of the wavelength ranges for the current spectra are the same. In some implementations, some of the widths of the wavelength ranges for the current spectra are different.

Current characteristic values for the selected peak are extracted from the modified wavelength ranges (step 1010), and the current characteristic values are compared to the target characteristic values (step 1012) using the endpoint determination logic discussed above in the context of FIG. 8. For example, a sequence of values for the current feature characteristic is determined from the sequence of spectra and a function is fit to the sequence of values. The function can be, for example, a linear function that can approximate the amount of material removed from the substrate during polishing based on the difference between the current characteristic value and the initial characteristic value.

As long as the endpoint determination logic determines that the endpoint condition has not been met ("no" branch of step 1014), polishing is allowed to continue, and steps 1006, 1008, 1010, 1012, and 1014 are repeated as appropriate. For example, endpoint determination logic determines, based on the function, that the target difference for the feature characteristic has not yet been reached.

In some implementations, when spectra of reflected light from multiple portions of the substrate are measured, the endpoint determination logic can determine that the polishing rate of one or more portions of the substrate needs to be adjusted so that polishing of the multiple portions is completed at, or closer to the same time.

When the endpoint determination logic determines that the endpoint condition has been met ("yes" branch of step 1014), an endpoint is called, and polishing is stopped (step 1016).

Spectra can be normalized to remove or reduce the influence of undesired light reflections. Light reflections contributed by media other than the film or films of interest include light reflections from the polishing pad window and from the base silicon layer of the substrate. Contributions from the window can be estimated by measuring the spectrum of light received by the in-situ monitoring system under a dark condition (i.e., when no substrates are placed over the in-situ monitoring system). Contributions from the silicon layer can be estimated by measuring the spectrum of light reflecting of a bare silicon substrate. The contributions are usually obtained prior to commencement of the polishing step. A measured raw spectrum is normalized as follows:

$$\text{normalized spectrum} = (A - \text{Dark})/(\text{Si} - \text{Dark})$$

where A is the raw spectrum, Dark is the spectrum obtained under the dark condition, and Si is the spectrum obtained from the bare silicon substrate.

In the described embodiment, the change of a wavelength peak in the spectrum is used to perform endpoint detection. The change of a wavelength valley in the spectrum (that is, local minima) also can be used, either instead of the peak or in conjunction with the peak. The change of multiple peaks (or valleys) also can be used when detecting the endpoint. For example, each peak can be monitored individually, and an endpoint can be called when a change of a majority of the peaks meet an endpoint condition. In other implementations, the change of an inflection point or an spectral zero-crossing can be used to determine endpoint detection.

Embodiments of the invention and all of the functional operations described in this specification can be implemented in digital electronic circuitry, or in computer software, firmware, or hardware, including the structural means disclosed in this specification and structural equivalents thereof, or in combinations of them. Embodiments of the invention can be implemented as one or more computer program products, i.e., one or more computer programs tangibly embodied in an information carrier, e.g., in a machine-readable storage device or in a propagated signal, for execution by, or to control the operation of, data processing apparatus, e.g., a programmable processor, a computer, or multiple processors or computers. A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

The above described polishing apparatus and methods can be applied in a variety of polishing systems. Either the polishing pad, or the carrier head, or both can move to provide relative motion between the polishing surface and the substrate. For example, the platen may orbit rather than rotate. The polishing pad can be a circular (or some other shape) pad secured to the platen. Some aspects of the endpoint detection system may be applicable to linear polishing systems, e.g., where the polishing pad is a continuous or a reel-to-reel belt that moves linearly. The polishing layer can be a standard (for example, polyurethane with or without fillers) polishing material, a soft material, or a fixed-abrasive material. Terms of relative positioning are used; it should be understood that the polishing surface and substrate can be held in a vertical orientation or some other orientation.

Particular embodiments of the invention have been described. Other embodiments are within the scope of the following claims. For example, the actions recited in the claims can be performed in a different order and still achieve desirable results.

What is claimed is:

1. A chemical mechanical polishing system, comprising:
a platen to hold a polishing pad;
a carrier head to hold a substrate in contact with the polishing pad;
an in-situ optical monitoring system configured to measure a sequence of spectra of light from the substrate while the substrate is being polished; and
a controller configured to
receive an identification of a selected spectral feature and a characteristic of the selected spectral feature to monitor during polishing,
receive the sequence of spectra of light from the in-situ monitoring system,
for at least some spectra in the sequence, dynamically generate a wavelength range based on a position of the spectral feature in a previous spectrum in the sequence of spectra,
for each spectrum of the at least some spectra in the sequence, search the dynamically generated wavelength range of the spectrum for the spectral feature and determine a value of the characteristic of the selected spectral to generate a sequence of values, and
determine at least one of a polishing endpoint or an adjustment for a polishing rate based on the sequence of values.

2. The polishing system of claim 1, wherein the dynamically generated wavelength range has a fixed width from spectrum to spectrum in the sequence of spectra.

3. The polishing system of claim 2, wherein the controller is configured to dynamically generate the wavelength range by centering the fixed width on the position of the spectral feature in the previous wavelength range.

4. The polishing system of claim 1, wherein the controller is configured to dynamically generate the wavelength range by determining the position of the spectral feature in the previous wavelength range and adjusting the wavelength range such that in a modified wavelength range the spectral feature is positioned closer to a center of the modified wavelength range.

5. The polishing system of claim 1, wherein the controller is configured to dynamically generate the wavelength range by determining a wavelength value for the selected spectral feature for the at least some of the spectra in the sequence of spectra to generate a sequence of wavelength values, fitting a function to the sequence of wavelength values, and calculating an expected wavelength value for the selected spectral feature for a subsequent spectrum measurement from the function.

6. The polishing system of claim 5, wherein the function is a linear function.

7. The polishing system of claim 1, wherein the selected spectral feature comprises a spectral peak, a spectral valley, or a spectral zero-crossing.

8. The polishing system of claim 7, wherein the characteristic comprises a wavelength, a width, or an intensity.

9. The polishing system of claim 8, wherein the selected spectral feature comprises a spectral peak and the characteristic comprises a peak width.

10. The polishing system of claim 1, wherein the controller is configured to determine at least one of the polishing endpoint or the adjustment for the polishing rate by fitting a function to the sequence of values and determining the at least one of the polishing endpoint or the adjustment for the polishing rate based on the function.

11. The polishing system of claim 10, wherein the controller is configured to determine the polishing endpoint by calculating an initial value of the characteristic from the function, calculating a current value of the characteristic from the function, and calculating a difference between the initial value and the current value, and ceasing polishing when the difference reaches a target difference.

12. The polishing system of claim 11, wherein the function is a linear function.

13. A chemical mechanical polishing control system, comprising:
    an in-situ optical monitoring system configured to measure a sequence of spectra of light from a substrate while the substrate is subjected to a polishing process; and
    a controller configured to
        receive an identification of a selected spectral feature and a characteristic of the selected spectral feature to monitor during polishing,
        receive the sequence of spectra of light from the in-situ monitoring system for a first portion of the polishing process,
        search an initial wavelength range of at least one spectrum from the sequence of spectra from the first portion of the polishing process for the spectral feature;
        generate an adjusted wavelength range based on a position of the spectral feature in a spectrum from the sequence of spectra from the first portion of the polishing process,
        receive the sequence of spectra of light from the in-situ monitoring system for a later second portion of the polishing process,
        search the adjusted wavelength range of at least one spectrum from the sequence of spectra from the second portion of the polishing process for the spectral feature and determine a value of the characteristic of the selected spectral feature in the at least one spectrum from the sequence of spectra from the second portion of the polishing process, and
        determine at least one of a polishing endpoint or an adjustment for a polishing rate based on the value.

14. The control system of claim 13, wherein the initial wavelength range and the adjusted wavelength range have the same width.

15. The control system of claim 14, wherein the controller is configured to generate the adjusted wavelength range by centering a fixed width on the position of the spectral feature in a spectrum from the sequence of spectra from the first portion of the polishing process.

16. The control system of claim 13, wherein the selected spectral feature comprises a spectral peak, a spectral valley, or a spectral zero-crossing.

17. The control system of claim 16, wherein the characteristic comprises a wavelength, a width, or an intensity.

18. The control system of claim 17, wherein the selected spectral feature comprises a spectral peak and the characteristic comprises a peak width.

19. The control system of claim 17, wherein the in-situ optical monitoring system comprises a sensor at a platen.

20. The control system of claim 19, wherein the controller is configured to receive the sequence of spectra for both the first portion and the second portion of the polishing process from the sensor of the in-situ optical monitoring system.

* * * * *